United States Patent [19]

Sato et al.

[11] Patent Number: 4,824,773
[45] Date of Patent: Apr. 25, 1989

[54] SILVER HALIDE COLOR PHOTOGRAPHIC MATERIAL

[75] Inventors: Shingo Sato; Yoshisada Nakamura; Koji Tamoto, all of Kanagawa, Japan

[73] Assignee: Fuji Photo Film Co., Ltd., Kanagawa, Japan

[21] Appl. No.: 41,560

[22] Filed: Apr. 23, 1987

[30] Foreign Application Priority Data

Apr. 23, 1986 [JP] Japan .................................. 61-94042

[51] Int. Cl.$^4$ ................................................. G03C 7/36
[52] U.S. Cl. .................................... 430/557; 430/389; 430/548
[58] Field of Search ................ 430/557, 389, 556, 548

[56] References Cited

U.S. PATENT DOCUMENTS

| | | | |
|---|---|---|---|
| 3,884,700 | 5/1975 | Quaglia | 430/557 |
| 4,401,752 | 8/1983 | Lau | 430/557 |
| 4,444,870 | 4/1984 | Hirano et al. | 430/557 |
| 4,511,649 | 4/1985 | Ogawa et al. | 430/557 |
| 4,587,207 | 5/1986 | Tsuda et al. | 430/557 |

*Primary Examiner*—Paul R. Michl
*Assistant Examiner*—Mark R. Buscher
*Attorney, Agent, or Firm*—Sughrue, Mion, Zinn, Macpeak & Seas

[57] ABSTRACT

A silver halide color photographic material comprising a support having thereon at least a silver halide emulsion layer containing a compound represented by formula (I)

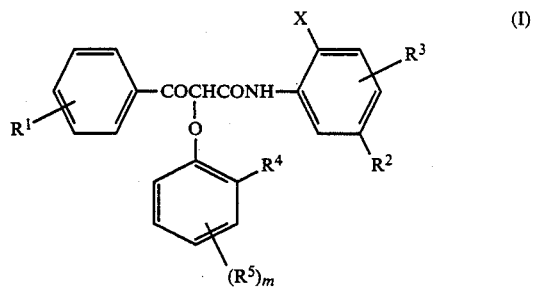

wherein $R^1$ and $R^2$ each represents a hydrogen atom, an alkyl group, an alkoxy group, a halogen atom, an alkoxycarbonyl group, a carbamoyl group, a carbonamido group, a sulfonamido group, or a sulfamoyl group; $R^3$ represents a hydrogen atom, a halogen atom, an alkyl group, an alkoxy group, or a carbonamido group; X represents a halogen atom or an alkoxy group; $R^4$ represents a carbamoyl group, an alkylsulfonyl group, an arylsulfonyl group, or a sulfamoyl group; $R^5$ represents a hydrogen atom, a halogen atom, a halogen-substituted alkyl group, a nitro group, a cyano group, a carbamoyl group, a sulfamoyl group, an alkylsulfonyl group, an acyl group, an alkoxycarbonyl group, an aryloxycarbonyl group, an alkoxy group, an aryloxy group, a carbonamido group, or a sulfonamido group; provided that at least one of said $R^1$, $R^2$, and $R^5$ is a non-diffusible group; and m represents an integer of from 0 to 4.

12 Claims, No Drawings

SILVER HALIDE COLOR PHOTOGRAPHIC MATERIAL

FIELD OF THE INVENTION

This invention relates to a silver halide color photographic materials containing photographic couplers, and in particular, to novel two-equivalent yellow couplers having excellent coloring properties.

BACKGROUND OF THE INVENTION

In the field of color photographic light-sensitive materials, extensive research have been made for increasing the coloring speed of couplers. In particular, for photographing (or in-camera) light-sensitive materials, the need for high-coloring couplers is high for increasing the apparent sensitivity and the image quality of the light-sensitive materials. If the reactivity of couplers to the oxidation product of a color developing agent is high, the sensitivity of the color photographic material containing the couplers is high. Also, when the reactivity of couplers is high, if a particularly high sensitivity is not required for the color photographic material, the amounts of the couplers and silver halide can be reduced. As a result thereof, the thickness of the silver halide emulsion layers can be reduced, to thus reduce light scattering of incident light. In other words, the sharpness of the color images obtained can be improved.

Conventional yellow-dye-forming couplers (hereinafter also referred to more simply as "yellow couplers") having a relatively high coloring property include the couplers described in U.S. Pat. Nos. 4,401,752, 4,511,649, and 4,587,207. However, the couplers disclosed in the aforesaid publications are still insufficient in one respect or another, e.g., the coupling reactivity is insufficient, the amount of the coupler must be increased due to low coloring density, etc., and hence further improvements in yellow couplers have been desired.

SUMMARY OF THE INVENTION

An object of this invention is to provide a color photographic material having high sensitivity and which provides high quality images by using yellow coupler(s) having high reactivity.

It has now been discovered that the aforesaid object can be attained by using the yellow coupler represented by formula (I) described below.

Thus, according to the present invention, there is provided a silver halide color photographic material comprising a support having thereon at least a silver halide emulsion layer containing a yellow coupler represented by formula (I)

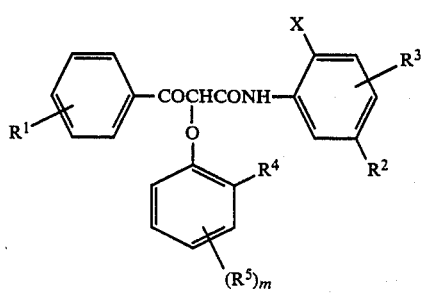

(I)

wherein $R^1$ and $R^2$ each represents a hydrogen atom, an alkyl group, an alkoxy group, a halogen atom, an alkoxycarbonyl group, a carbamoyl group, a carbonamido group, a sulfonamido group, or a sulfamoyl group; $R^3$ represents a hydrogen atom, a halogen atom, an alkyl group, an alkoxy group, or a carbonamido group; X represents a halogen atom or an alkoxy group; $R^4$ represents a carbamoyl group, an alkylsulfonyl group, an arylsulfonyl group, or a sulfamoyl group; $R^5$ represents a hydrogen atom, a halogen atom, a halogen-substituted alkyl group, a nitro group, a cyano group, a carbamoyl group, a sulfamoyl group, an alkylsulfonyl group, an acyl group, an alkoxycarbonyl group, an aryloxycarbonyl group, an alkoxy group, an aryloxy group, a carbonamido group, or a sulfonamido group; provided that at least one of said $R^1$, $R^2$, and $R^5$ is a non-diffusible group (which may include a polymer chain); and m represents an integer of from 0 to 4.

DETAILED DESCRIPTION OF THE INVENTION

The yellow couplers represented by formula (I) are explained in more detail below.

In formula (I), $R^1$ preferably represents a hydrogen atom, a halogen atom, an alkyl group, an alkoxy group, a carbonamido group, or a sulfonamido group. $R^2$ preferably represents a hydrogen atom, a halogen atom, a carbonamido group, a sulfonamide group, an alkoxycarbonyl group, a carbamoyl group, or a sulfamoyl group and is particularly preferably a carbonamido group, a sulfonamido group, an alkoxycarbonyl group, a carbamoyl group, or a sulfamoyl group. X preferably represents a halogen atom or an alkoxy group having from 1 to 4 carbon atoms, and is more preferably a chlorine atom, a methoxy group, or an ethoxy group. $R^3$ preferably represents a hydrogen atom, a halogen atom, an alkyl group having from 1 to 4 carbon atoms, an alkoxy group, or a carbonamido group and is more preferably a hydrogen atom, a chlorine atom, a methyl group, a methoxy group, or an ethoxy group. $R^4$ preferably represents a carbamoyl group having from 1 to 10 carbon atoms, an alkylsulfonyl group, an arylsulfonyl group, or a sulfamoyl group and is more preferably a methylsulfonyl group, an ethylsulfonyl group, or a phenylsulfonyl group. Also, $R^5$ preferably represents a hydrogen atom, a chlorine atom, $-CF_3$, a nitro group, a cyano group, a carbamoyl group, a sulfamoyl group, an alkylsulfonyl group, an alkylcarbonyl group, an alkoxycarbonyl group, an aryloxycarbonyl group, or an alkoxy, aryloxy, carbonamido, or sulfonamido group linked to the meta position via the oxygen atom of the aryloxy releasing group.

Furthermore, m is an integer of from 0 to 4, preferably from 0 to 3, and when m is 2, 3 or 4, said $R^5$ groups may be the same or different.

In formula (I), however, at least one of said $R^1$, $R^2$, and $R^5$ is a non-diffusible group, and the non-diffusible group is one of the aforesaid groups further containing an alkyl group or an alkenyl group each having from 8 to 32 carbon atoms.

The couplers represented by formula (I) described above may form a dimer or higher oligomer by bonding to each other through a divalent or more group at $R_1$, $R_2$ or $R_3$. In this case, the carbon atom number defined above for the aforesaid group may be outside of the defined range.

When the couplers represented by formula (I) form an oligomer, a homopolymer, or a copolymer of an addition polymerizable ethylenically unsaturated compound (yellow coloring monomer) having a yellow dye-forming coupler residue is a typical example thereof. In this case, the oligomer, etc. contains a recurring unit represented by formula (II) described below, and the recurring unit represented by formula (II) may be included in the oligomer as one or more kinds thereof, or the oligomer may be a copolymer containing one or more kinds of non-coloring ethylenical monomers as the copolymerizing component(s).

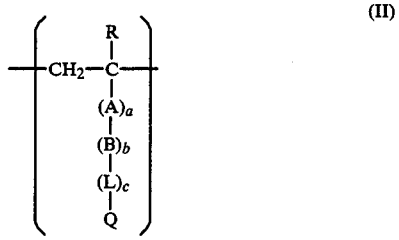

wherein R represents a hydrogen atom, an alkyl group having from 1 to 4 carbon atoms, or a chlorine atom; A represents —CONH—, —COO—, or a substituted or unsubstituted phenylene group; B represents a substituted or unsubstituted alkylene group, a substituted or unsubstituted phenylene group, or a substituted or unsubstituted aralkylene group; L represents —CONH—, —NHCONH—, —NHCOO—, —NHCO—, —OCONH—, —NH—, —COO—, —OCO—, —CO—, —O—, —S—, —SO$_2$—, —NHSO$_2$—, or —SO$_2$NH—; Q represents a yellow coupler residual group formed by releasing hydrogen atoms other than the hydrogen atom of the methine group from the compound represented by formula (I) described above; and a, b, and c each represents 0 or 1.

As the oligomer, a copolymer of a yellow coloring monomer providing the coupler unit represented by formula (II) described above and a non-coloring ethylenical monomer as described below is preferred.

Examples of the non-coloring ethylenical monomer which does not cause coupling with the oxidation product of an aromatic primary amine developing agent include acrylic acid, α-chloroacrylic acid, α-alkylacrylic acid (e.g., methacrylic acid), the esters or amides induced from these acrylic acids (e.g., acrylamide, methacrylamide, n-butylacrylamide, t-butylacrylamide, diacetoneacrylamide, methyl acrylate, ethyl acrylate, n-propyl acrylate, n-butyl acrylate, t-butyl acrylate, iso-butyl acrylate, 2-ethylhexyl acrylate, n-octyl acrylate, lauryl acrylate, methyl methacrylate, ethyl methacrylate, n-butyl methacrylate, and β-hydroxy methacrylate), vinyl esters (e.g., vinyl acetate, vinyl propionate, and vinyl laurate), acrylonitrile, methacrylonitrile, aromatic vinyl compounds (e.g., styrene and the derivatives thereof, such as vinyltoluene, divinylbenzene, vinylacetophenone, and sulfostyrene), itaconic acid, citraconic acid, crotonic acid, vinylidene chloride, vinyl alkyl ethers (e.g., vinyl ethyl ether), maleic acid esters, N-vinyl-2-pyrrolidone, N-vinylpyridine, and 2- and 4-vinylpyridines.

In particular, acrylic acid esters, methacrylic acid esters, and maleic acid esters are preferred as the non-coloring ethylenical monomers. The monomers may be used singly or as a mixture thereof. Examples include a combination of methyl acrylate and butyl acrylate, butyl acrylate and styrene, butyl methacrylate and methacrylic acid, and methyl acrylate and diacetoneacrylamide.

As is well known in the field of polymeric couplers, the ethylenically unsaturated monomer which is copolymerized with the vinylic monomer corresponding to the recurring unit shown by formula (II) described above is selected so that the physical properties and/or the chemical properties of the copolymer formed, such as the solubility, the compatibility with a binder for the photographic colloid composition (e.g., gelatin), the softening temperature, the flexibility, the heat stability, etc., are imparted with good influences.

The yellow polymer coupler for use in this invention may be prepared by emulsion dispersing an organic solvent solution of an oleophilic polymer coupler obtained by the polymerization of a vinylic monomer giving the coupler unit shown by formula (II) in an aqueous gelatin solution as the form of latex or by a direct emulsion polymerization of the vinylic monomer described above.

For dispersing by emulsification the oleophilic polymer coupler in an aqueous gelatin solution as the form of latex, the methods described in U.S. Pat. No. 3,451,820 can be used and for the emulsion polymerization, the method described in U.S. Pat. Nos. 4,080,211 and 3,370,952 can be used.

The yellow couplers represented by formula (II) described above can be applied to a multilayer multicolor photographic material having at least three emulsion layers each having a different spectral sensitivity on a support. A multilayer natural color photographic material usually has at least one red-sensitive emulsion layer, at least one green-sensitive emulsion layer, and at least one blue-sensitive emulsion layer on a support. The disposition order of these emulsion layers can be optionally selected according to requirement. Also, the coupler of formula (I) can be used for a light-sensitive silver halide emulsion layer such as a high speed silver halide emulsion layer and a intermediate speed silver halide emulsion layer, or an adjacent layer thereto.

The amount of the coupler of formula (I) for use in this invention depends upon the structure of the compound and the use thereof, but is preferably from $1 \times 10^{-7}$ to 1 mol, and more preferably from $1 \times 10^{-3}$ to 0.5 mol, per mol of silver in the emulsion layer when the compound exists in the same emulsion layer or of silver in the emulsion layer adjacent to the layer containing the compound.

The coupler(s) of formula (I) for use in this invention may be used in a certain layer such as a silver halide emulsion layer, singly or together with other known coupler(s).

Specific examples of the aryloxy releasing group of the yellow coupler for use in this invention represented by formula (I) are illustrated below, but the invention is not limited to these groups.

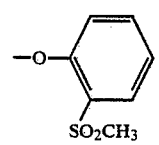

-continued
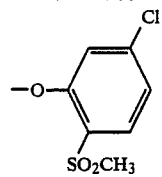
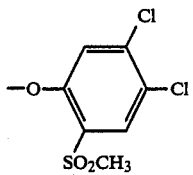
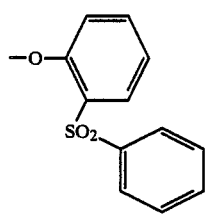
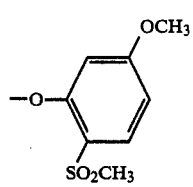
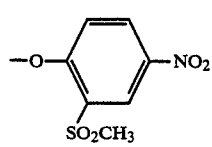
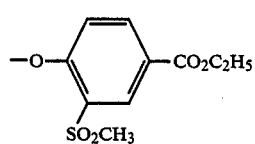
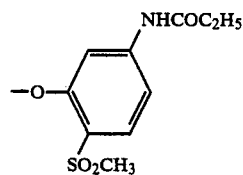
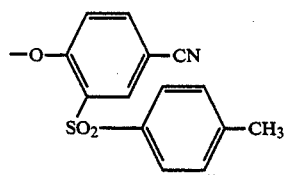
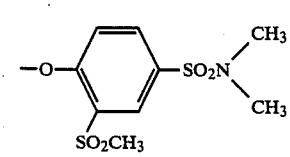
-continued
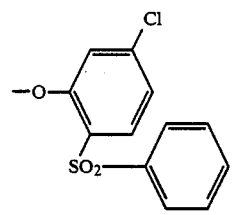
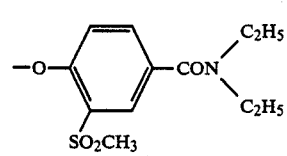
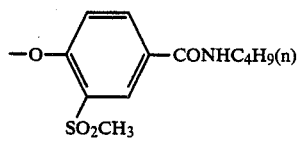
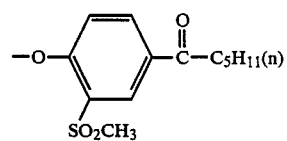
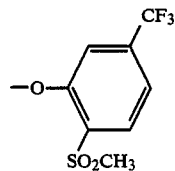
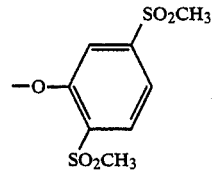
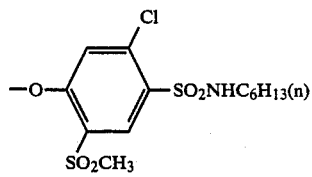
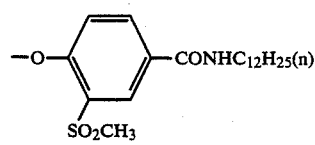
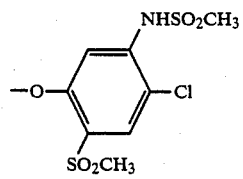

-continued
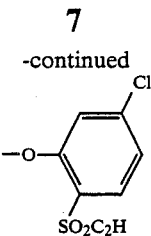
Specific examples of the yellow two-equivalent coupler for use in this invention represented by formula (I) described above are illustrated below, but the couplers in this invention are not limited to these groups.
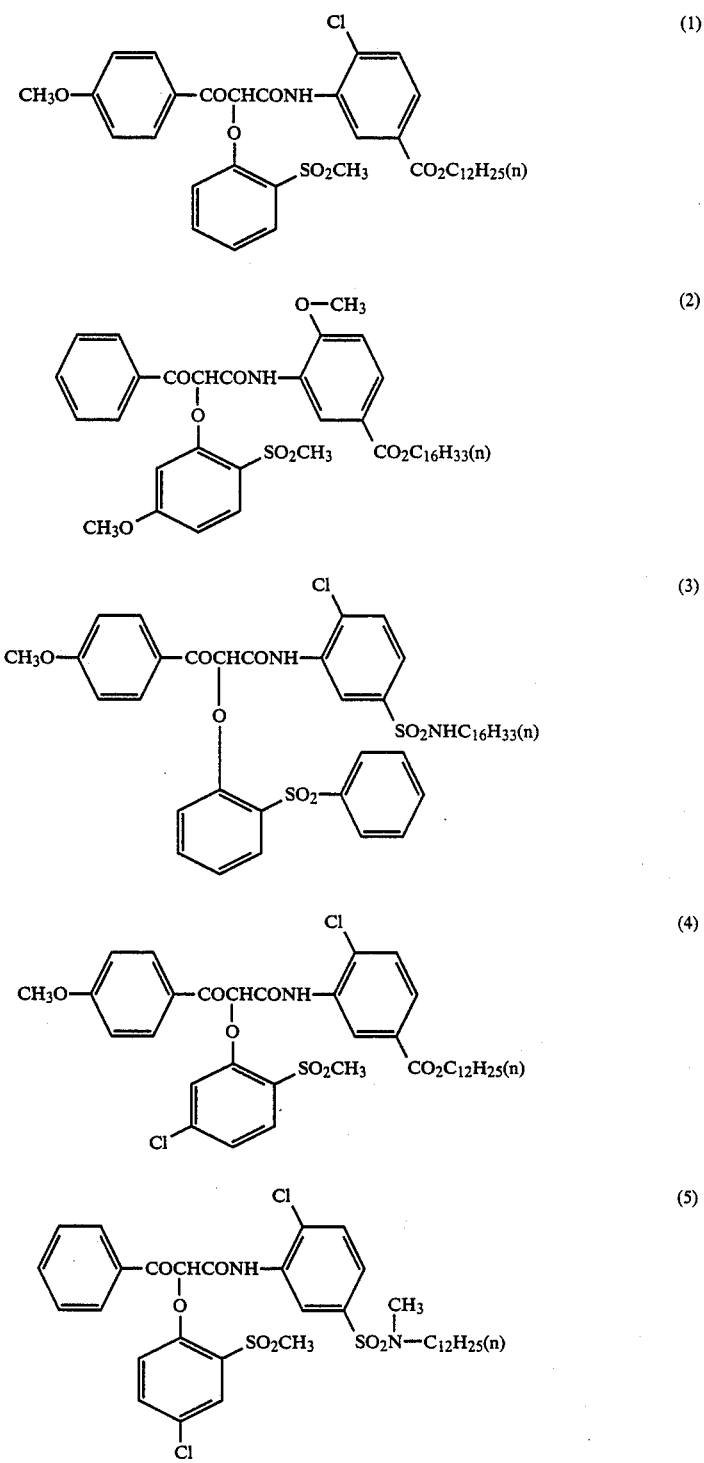

-continued
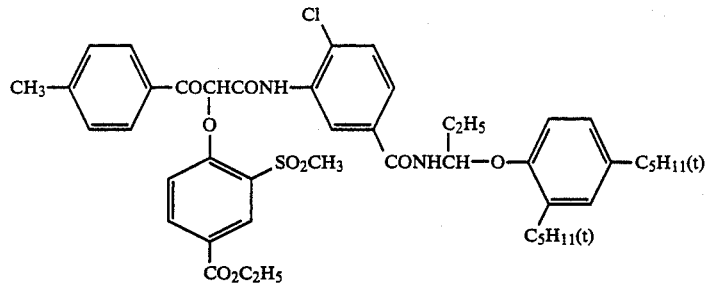  (6)
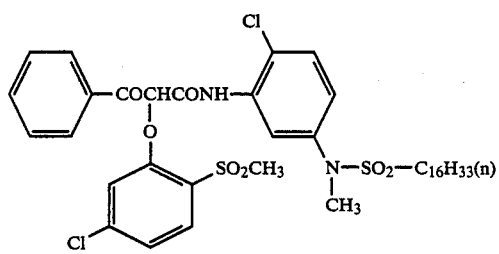  (7)
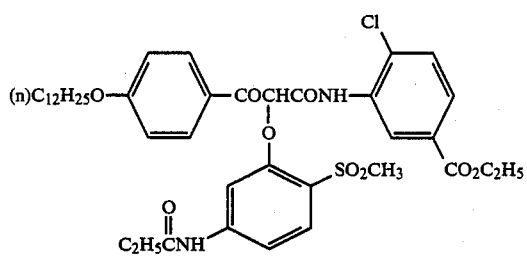  (8)
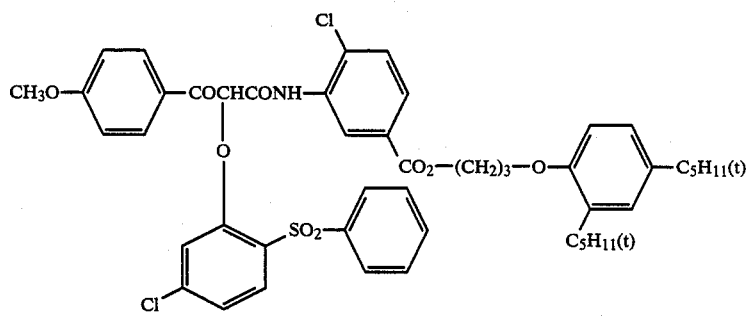  (9)
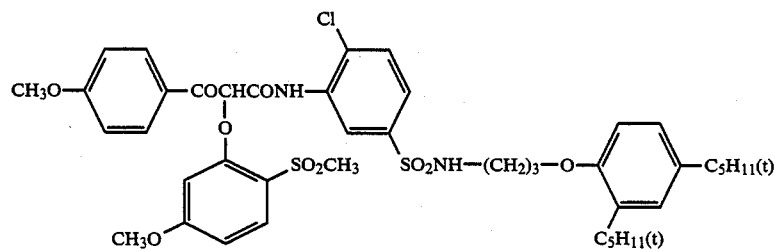  (10)
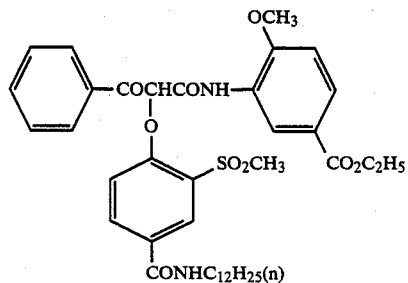  (11)

-continued
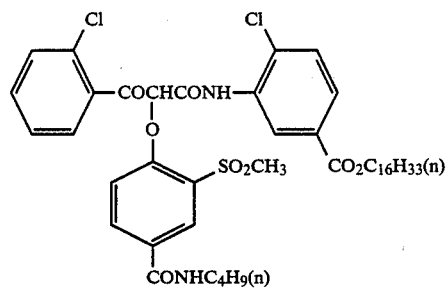
(12)
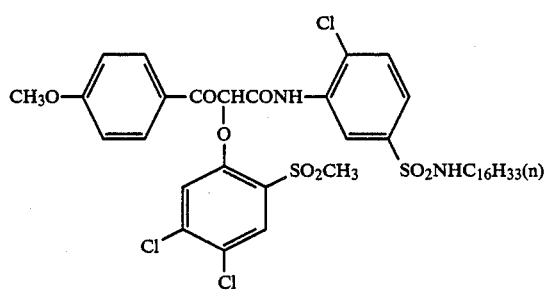
(13)
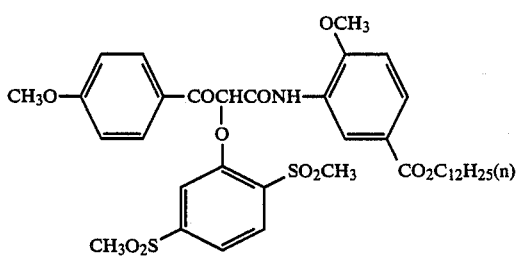
(14)
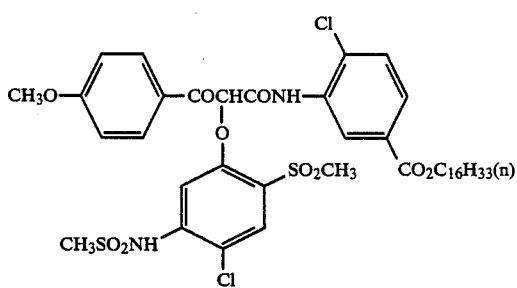
(15)
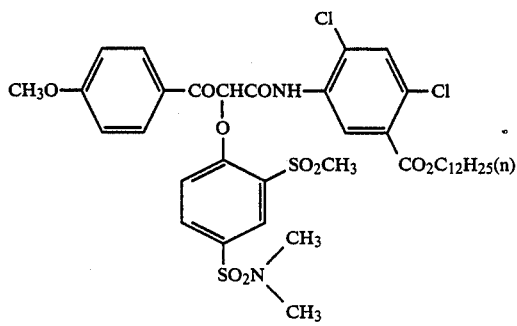
(16)

-continued
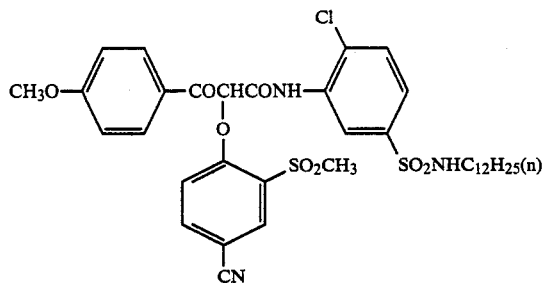
(17)
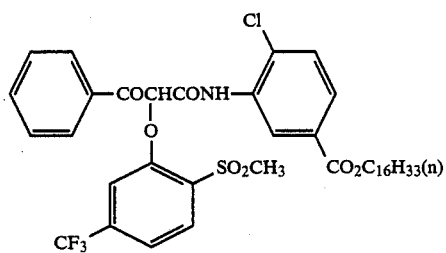
(18)
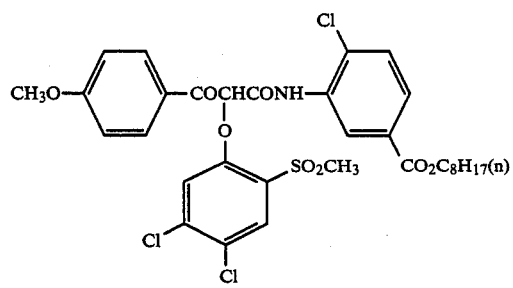
(19)
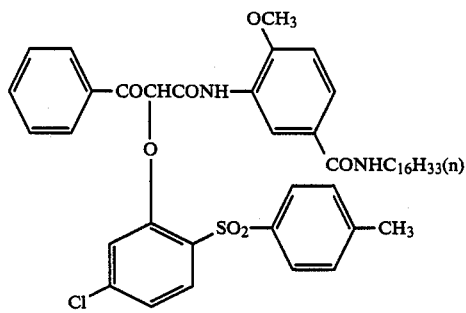
(20)
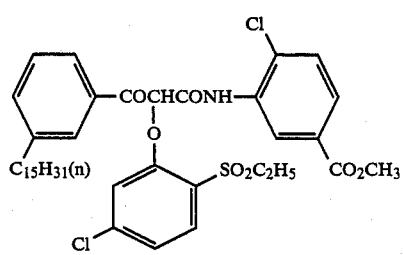
(21)

-continued
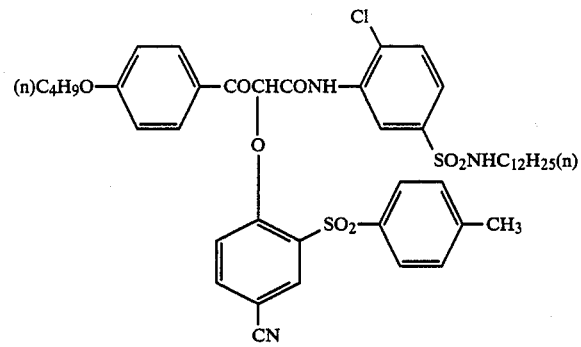
(22)
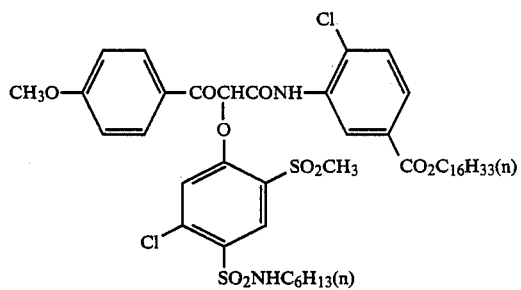
(23)
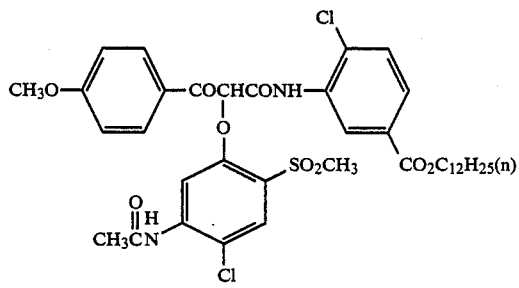
(24)
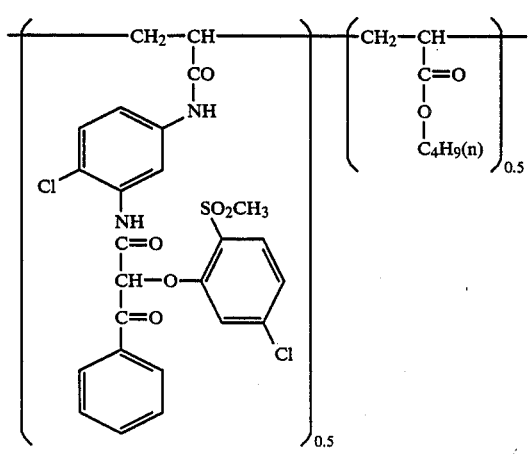
(25)

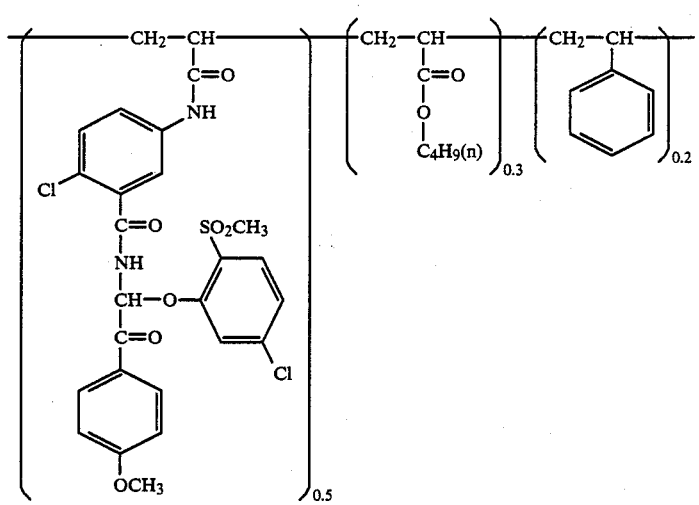

(26)

The yellow two-equivalent couplers for use in this invention shown by formula (I) are produced from corresponding four-equivalent couplers by the reaction shown by the following reaction formula.

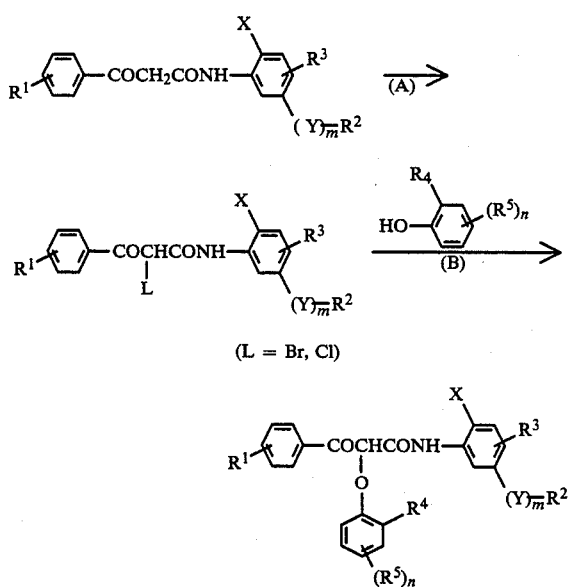

(L = Br, Cl)

In reaction (A) shown in the above reaction formula, the halide can be obtained at a high yield by using, for example, bromine or N-bromosuccinic acid imide in the case of the bromation, or by using, for example, sulfuryl chloride or chlorine in the case of the chlorination. In these cases, it is preferred to perform the reaction in a halogen series solvent such as dichloromethane, chloroform, dichloroethane, etc., as the reaction solvent.

In reaction (B) shown in the reaction formula, the desired coupler can be obtained by reacting the halide and the phenol derivative in the existence of a base in a solvent such as dichloromethane, chloroform, dichloroethane, acetonitrile, dimethylformamide, dimethylacetamide, tetrahydrofuran, toluene, etc. In this case, as the base, sodium hydroxide, potassium hydroxide, potassium carbonate, triethylamine, N-methylpiperidine, pyridine, DBN (1,5-diazabicyclo[4,3,0]non-5-ene), DBU (1,8-diazabicyclo[5,4,0]undeca-7-ene), etc. Phenols can be used for the reaction as alkaline metal salts.

Also when the yellow coupler for use in this invention is a polymer coupler [shown by formula (II) described above], the coupler can be produced according to the method described, for example, in British Pat. No. 2,127,984.

Examples of the production of specific examples of the yellow coupler for use in this invention are described below.

SYNTHESIS EXAMPLE 1: SYNTHESIS OF COMPOUND (1)

In 200 ml of chloroform was dissolved 55 g of α-chloro-α-(p-methoxybenzoyl)-2-chloro-5-dodecyloxycarbonylacetanilide obtained by the reaction of α-(p-methoxybenzoyl)-2-chloro-5-dodecyloxycarbonylacetanilide and sulfuryl chloride, the solution thus obtained was added dropwise to a mixture of 20.7 g of o-methylsulfonylphenol, 16 ml of triethylamine, and 200 ml of acetonitrile at room temperature over a period of 30 minutes, and the resultant mixture was stirred for 20 hours.

The reaction mixture was poured in an aqueous solution of 50 g of sodium hydroxide in 500 ml of water and the product was extracted with 500 of methylene chloride. The organic solvent layer (extract) thus formed was collected, washed with an aqueous 3% hydrochloric acid solution and then water, and then dried by sodium sulfate.

Then the methylene chloride solvent was distilled off under reduced pressure to provide 71 g of an oily material, which was purified by silica gel column chromatography (2.5 kg of silica gel, eluent: a 3/1 mixture of n-hexane and ethyl acetate) and then recrystallized from ethanol to provide 47 g of the desired compound (1).

The results of the elemental analysis of the product were as follows.

Elemental Analysis

|  | C | H | N |
|---|---|---|---|
| Found: | 63.25% | 6.52% | 2.01% |
| Calculated: | 63.0% | 6.46% | 2.04% |

SYNTHESIS EXAMPLE 2: SYNTHESIS OF COMPOUND (3)

In 250 ml of chloroform was dissolved 64 g of α-chloro-α-(p-methoxybenzoyl)-2-chloro-5-hexadecylsulfamoylacetanilide prepared by the reaction of α-(p-methoxybenzoyl)-2-chloro-5-hexadecylsulfamoylacetanilide and sulfuryl chloride and the solution was added to a mixture of 28.1 g of o-phenylsulfonylphenol, 16 ml of triethylamine, and 200 ml of acetonitrile at room temperature. After reacting for 30 minutes, the reaction mixture obtained was poured into 500 ml of an aqueous solution of 50 g of sodium hydroxide in 500 ml of water and the product was extracted with 500 ml of methylene chloride. The organic solvent layer thus formed was collected, washed with an aqueous 3% hydrochloric acid solution and then water, and then dried by sodium sulfate.

The methylene chloride solvent was distilled off from the extract under reduced pressure and the oily residue thus formed was purified by silica gel column chromatography as in Synthesis Example 1 and recrystallized from ethanol to provide 41 g of Compound (3). The results of the elemental analysis of the product were as follows.

Elemental Analysis

|  | C | H | N |
|---|---|---|---|
| Found: | 63.17% | 6.64% | 3.29% |
| Calculated: | 62.95% | 6.60% | 3.30% |

SYNTHESIS EXAMPLE 3: SYNTHESIS OF COMPOUND (4)

A solution of 55 g of α-chloro-α-(p-methoxybenzoyl)-2-chloro-5-dodecyloxycarbonylacetanilide dissolved in 200 ml of chloroform was added to a mixture of 25 g of 5-chloro-2-methylsulfonylphenol, 16 ml of triethylamine, and 200 ml of acetonitrile at room temperature and the resultant mixture was stirred for 24 hours. The reaction mixture obtained was treated as in synthesis Example 1. Then, the concentrated residue of the extract thus formed was purified using silica gel column chromatography as in Synthesis Example 1 and crystallized from methanol and ethyl acetate to provide 38 g of the desired Compound (4) having melting point of 109° C. to 111° C.

Elemental Analysis

|  | C | H | N |
|---|---|---|---|
| Found: | 60.21% | 6.08% | 1.92% |
| Calculated: | 59.99% | 6.01% | 1.94% |

As the silver halide for the photographic silver halide emulsion layers of the color photographic material of this invention, silver bromide, silver iodobromide, silver iodochlorobromide, silver chlorobromide, or silver chloride may be used. A preferred silver halide is silver iodobromide or silver iodochlorobromide containing less than about 30 mol% silver iodide and a particularly preferred silver halide is silver iodobromide containing from about 2 mol% to 25 mol% silver iodide.

The silver halide grains for the photographic emulsion layers in this invention may have a so-called regular crystal form such as cubic, octahedral, tetradecahedral, etc., an irregular crystal form such as spherical, etc., a crystal form having a crystal defect such as a twinning plane, etc., or composite forms thereof.

The grain size of the silver halide for use in this invention may be as fine as less than about 0.1 μm, or as large as up to about 10 μm in the diameter of the projected area thereof. Furthermore, the silver halide emulsion may be a monodisperse emulsion having a narrow size distribution of silver halide grains or a polydisperse emulsion having a wide size distribution of silver halide grains.

The silver halide photographic emulsions for use in this invention can be produced by the methods described, for example, in *Research Disclosure*, RD No. 17643, pp. 22–23 (December 1978), "J. Emulsion Preparation and Types" and ibid., RD No. 18716, page 648 (November 1979), P. Glafkides, *Chimie et Physique Photographique*, pp. 329–425, Paul Montel (1967); G. F. Duffin, *Photographic Emulsion Chemistry*, pp. 57–82, Focal Press (1966); V. Z. Zelikman et al, *Making and Coating Photographic Emulsion*, pp. 69–87, Focal Press (1964), etc. That is, an acid method, a neutral method, an ammonia method, etc., can be used for producing the emulsions.

Also, as a method for reacting a soluble silver salt and a soluble halide, a single jet method, a double jet method, or a combination thereof may be used. Furthermore, a so-called back mixing method of forming silver halide grains in the existence of excessive silver ions can be used. As one of the double jet method, a so-called controlled double jet method of keeping a constant pAg in the liquid phase for forming silver halide grains can be used, and according to such method, a silver halide emulsion containing silver halide grains having a regular crystal form and almost uniform grain sizes can be obtained.

A mixture of two or more kinds of silver halide emulsions separately prepared may be also used.

A silver halide emulsion composed of the regular silver halide grains described above can be obtained by controlling pAg and pH of the system during the formation of the silver halide grains. More specifically, the silver halide emulsion of this type can be prepared by the methods described, for example, in *Photographic Science and Engineering*, Vol. 6, 159–165 (1962), *Journal of Photographic Science*, Vol. 12, 242–251 (1964), U.S. Pat. No. 3,655,394, and British Pat. No. 1,413,748.

A typical monodisperse silver halide emulsion is an emulsion wherein the mean grain size of the silver halide grains is larger than about 0.1 μm and at least about 95% by weight of the silver halide grains are in the range of ±40% of the mean grain size. A monodisperse silver halide emulsion wherein the mean grain size of the silver halide grains is from about 0.25 μm to about 2 μm and at least about 95% by weight or at least 95% by number are in the range of ±20% of the mean grain size can be used in this invention. Such a monodisperse emulsion can be produced by the methods described, for example, in U.S. Pat. Nos. 3,574,628, 3,655,394, and British Pat. No. 1,413,748. Furthermore, the monodisperse emulsions described in Japanese Patent Application (OPI) Nos. 8600/73, 39027/76, 83097/76, 137133/78, 48521/79, 99419/79, 37635/83, 49938/83 (the term "OPI" as used herein means an "unexamined published application"), etc., can be preferably use in this invention.

Also, tabular silver halide grains having an aspect ratio of at least about 5 can be used in this invention. Tabular silver halide grains can be easily prepared by the methods described in Gutoff, *Photographic Science and Engineering*, Vol. 14, 248–257 (1970), U.S. Pat. Nos. 4,434,226, 4,414,310, 4,433,048, 4,439,520, British Pat. No. 2,112,157. The use of such a tabular grain silver halide emulsion provides advantages such as the increase of the color sensitizing effect by sensitizing dye(s), the improvement of graininess, the increase of sharpness, etc., as described in U.S. Pat. No. 4,434,266, etc., cited above.

The crystal structure of the silver halide grains for use in this invention may have a uniform halogen composition throughout the grain, a different halogen composition between the inside and the layer portion thereof, or a layer structure. These silver halide emulsions are disclosed in British Pat. No. 1,207,146, U.S. Pat. Nos. 3,505,068, 4,444,877, and Japanese Patent Application (OPI) No. 143331/85.

Also, The silver halide grains may be composed of silver halide grains having different compositions joined to each other by epitaxial junction, or may be joined to salts or compounds other than silver halide, such as silver rhodanate, lead oxide, etc. The emulsions composed of these silver halide grains are disclosed in U.S. Pat. Nos. 4,094,684, 4,142,900, 4,459,353, British Pat. No. 2,038,792, U.S. Pat. Nos. 4,349,622, 4,395,478, 4,433,501, 4,463,087, 3,656,962, 3,852,067, Japanese Patent Application (OPI) No. 162540/84, etc. Also, an emulsion composed of a mixture of silver halide grains having various crystal forms can be used.

The silver halide emulsions for use in this invention are usually subjected to physical ripening, chemical ripening, and spectral sensitization at use. Additives which are used in the aforesaid steps are described in *Research Disclosure*, RD No. 17643 and ibid., No. 18716, and the portions corresponding to these descriptions are shown in the following table.

Other photographic additives which can be also used for the described portions are also shown in the same table.

For the color photographic materials of this invention, various couplers can be used in addition to the yellow couplers represented by formula (I) described above. Specific examples of color couplers are described in the patents cited in *Research Disclosure*, RD No. 17643 (December 1978), VII-C to G. As dye-forming couplers, such couplers as giving three primary colors by subtractive color photography (i.e., yellow, magenta, and cyan) by color development are important and in addition to the non-diffusible four-equivalent and two-equivalent couplers described in the patents cited in above-described *Research Disclosure*, RD No. 17643, VII-C and D and the yellow couplers shown by formula (I) described above, the following couplers can be also preferably used.

In this invention, as yellow couplers, the two-equivalent couplers shown by formula (I) described above are used as described hereinbefore, but, if desired, yellow couplers as described below may be used together with the aforesaid yellow couplers.

As the yellow couplers which may be used, if desired, together with the above-described yellow couplers of formula (I), there are hydrophobic acylacetamide series couplers having a ballast group. Specific examples thereof are described in U.S. Pat. Nos. 2,407,210, 2,875,057 and 3,265,506. As such yellow couplers, two-equivalent yellow couplers are also preferred and typical examples thereof are oxygen atom releasing type yellow couplers described in U.S. Pat. Nos. 3,408,194, 3,447,928, 3,933,501 and 4,022,620, and nitrogen atom releasing type yellow couplers as described in Japanese Patent Publication No. 10739/83, U.S. Pat. Nos. 4,401,752, 4,326,024, *Research Disclosure*, RD No. 18053 (April 1979), British Pat. No. 1,425,020, West German Patent Application (OLS) Nos. 2,219,917, 2,261,361, 2,329,587, and 2,433,812. In these couplers, α-pivaloylacetanilide series couplers are excellent in fastness, in particular, light fastness of the colored dyes formed, while α-benzoylacetanilide series couplers provide dyes having high coloring density.

As magenta couplers for use in this invention, there are hydrophobic indazolone series and cyanoacetyl series couplers having a ballast group and further 5-pyrazolone series and pyrazoloazole series couplers are preferred.

As the 5-pyrazolone series couplers, couplers wherein the 3-position is substituted by an arylamino group or an acylamino group are preferred from the viewpoints of the hue of the colored dyes and the coloring density. Specific examples of these magenta couplers are described in U.S. Pat. Nos. 2,311,082, 2,343,703, 2,600,788, 2,908,573, 3,062,653, 3,152,896, and 3,936,015. As the releasable group for the two-equivalent 5-pyrazolone series magenta couplers, nitrogen atom releasing groups as described in U.S. Pat. No. 4,310,619 and the arylthio group described in U.S. Pat. No. 4,351,897 are preferred. Also, the 5-pyrazolone

| Additive | RD 17643 | RD 18716 |
|---|---|---|
| 1 Chemical Sensitizer | page 23 | page 648, right column |
| 2 Sensitivity Increasing Agent | | same above |
| 3 Spectral Sensitizer, Super Color Sensitizer | pages 23–24 | page 648, right column to page 649, right column |
| 4 Whitening Agent | page 24 | — |
| 5 Antifoggant and Stabilizer | pages 24–25 | page 649, right column |
| 6 Light Absorbent, Filter Dye, Ultraviolet Absorbent | pages 25–26 | page 649, right column to page 650, left column |
| 7 Stain Preventing Agent | page 25, right column | page 650, left column to right column |
| 8 Dye Image Stabilizer | page 25 | — |
| 9 Hardening Agent | page 26 | page 651, left column |
| 10 Binder | page 26 | same as above |
| 11 Plasticizer, Lubricant | page 27 | page 650, right column |
| 12 Coating Aid, Surface Active Agent | pages 26–27 | same as above |
| 13 Antistatic Agent | page 27 | same as above | series couplers having a ballast group as described in European Pat. No. 73,636 provide dye having high coloring density.

Examples of pyrazolone series couplers include pyrazolobenzimidazoles described in U.S. Pat. No. 3,061,432 and preferably the pyrazolo[5,1-c][1,2,4]triazoles described in U.S. Pat. No. 3,725,067, the pyrazolotetrazoles described in *Research Disclosure*, RD No. 24220 (June 1984) and Japanese Patent Application (OPI) No. 33552/85 and the pyrazolopyrazoles described in *Research Disclosure*, RD No. 24230 (June 1984) and Japanese Patent Application (OPI) No. 43659/85. Also, the imidazo[1,2-b]pyrazoles described in U.S. Pat. No. 4,500,630 are preferred and the pyrazolo[1,5-b][1,2,4]triazoles described in U.S. Pat. No. 4,540,654 are more preferred from the viewpoint of less yellow side adsorption of the colored dyes and high light fastness thereof.

Cyan couplers for use in this invention include hydrophobic non-diffusible naphthol series and phenol series couplers.

Naphthol series couplers include the couplers described in U.S. Pat. No. 2,474,293, and preferably the oxygen atom releasing type two-equivalent naphthol series couplers described in U.S. Pat. Nos. 4,052,212, 4,146,396, 4,228,233 and 4,296,200.

Also, specific examples of the phenol series couplers which can be used in this invention are described in U.S. Pat. Nos. 2,369,929, 2,801,171, 2,772,162 and 2,895,826.

Cyan couplers capable of forming cyan dyes having high fastness to moisture and temperature are preferably used in this invention and typical examples of these cyan couplers are the phenol series couplers having an alkyl group having 2 or more carbon atoms at the meta-position of the phenol nucleus described in U.S. Pat. No. 3,772,002, the 2,5-diacylamino-substituted phenol series couplers described in U.S. Pat. Nos. 2,772,162, 3,758,308, 4,126,396, 4,334,011, 4,327,173, West German Patent Application (OLS) No. 3,329,729, and European Pat. No. 121,365, and the phenol series couplers having a phenylureido group at the 2-position and an acylamino group at the 5-position described in U.S. Pat. Nos. 3,446,622, 4,333,999, 4,451,559 and 4,427,767. The naphthol series cyan couplers having a sulfonamido group, an amido group, etc., at the 5-position of the naphthol nucleus described in European Pat. No. 161,626A are excellent in the fastness of the color images formed and are preferably used in this invention.

For correcting unnecessary absorption of colored dyes, it is preferred to perform masking by using a colored coupler together with the aforesaid coloring couplers for photographing (or in camera) color photographic materials. For example, there are the yellow-colored magenta couplers described in U.S. Pat. No. 4,163,670 and Japanese Patent Publication No. 39413/82 and the magenta-colored cyan couplers described in U.S. Pat. Nos. 4,004,929, 4,138,258, and British Pat. No. 1,146,368. Other colored couplers which can be used for the aforesaid purpose in this invention are described in *Research Disclosure*, RD No. 17643 (December 1978), VII-G.

The graininess of the color images formed can be improved by using a coupler providing a colored dye having a proper diffusibility together with the aforesaid color coupler(s). Specific examples of such couplers are described in U.S. Pat. No. 4,366,237 and British Pat. No. 2,125,570 for magenta couplers and in West German Patent Application (OLS) No. 3,234,533 and European Pat. No. 96,570 for yellow, magenta and cyan couplers.

The dye-forming couplers and the specific couplers described above may exist in the form a dimer or higher oligomer or polymer. Specific examples of the polymerized dye-forming coupler are described in U.S. Pat. Nos. 3,451,820 and 4,080,211. Also, specific examples of the polymerized magenta coupler are described in British Pat. No. 2,102,173 and U.S. Pat. No. 4,367,282.

Couplers releasing a photographically useful residue during coupling can be also preferably used in this invention. DIR (development inhibitor releasing) couplers releasing a development inhibitor with coupling described in the patents cited in *Research Disclosure*, RD No. 17643 (December 1978), VII-F can be advantageously used in this invention.

Examples of DIR couplers which are preferably used as a combination with the aforesaid color couplers in this invention are the developer inactivation type DIR couplers, the development inhibitor of which released is inactivated by the developer described in Japanese Patent Application (OPI) No. 151944/82, the timing DIR couplers releasing a development inhibitor which is accompanied by an intramolecular nucleating reaction after the release thereof described in U.S. Pat. No. 4,248,962 and Japanese Patent Application (OPI) No. 154234/82, and the reaction type DIR couplers releasing a reactive compound which forms a development inhibitor by a reaction in emulsion layer described in Japanese Patent Application (OPI) No. 184248/85. Particularly preferred DIR couplers are the developer inactivation type DIR couplers described in Japanese Patent Application (OPI) Nos. 151944/82, 217932/83, 218644/85, 225156/85 and 233650/85 and the reaction type DIR couplers described in Japanese Patent Application (OPI) No. 184248/85.

For the color photographic materials of this invention, couplers imagewise releasing a nucleating agent, a development inhibitor, or the precursor thereof at development can be used. Specific examples of such couplers are described in British Pat. Nos. 2,097,140 and 2,131,188. Couplers releasing a nucleating agent having an absorptive action for silver halide are particularly preferred and specific examples thereof are described in Japanese Patent Application (OPI) No. 157638/84 and U.S. Pat. No. 4,628,024.

Proper supports which can be used in this invention are described in *Research Disclosure*, RD No. 17643 (December 1978), page 28 and ibid., RD No. 18716, Page 647, right column to page 648, left column.

The color photographic materials of this invention can be photographically processed by the ordinary processes described in *Research Disclosure*, RD No. 17643 (December 1978), pages 28–29 and ibid., RD No. 18716 (November 1979), page 651, left column to right column.

The color developer which is used for developing the color photographic materials of this invention is an alkaline aqueous solution containing an aromatic primary amine color developing agent as the main component. As the color developing agent, an aminophenol series compound is advantageous, but a p-phenylenediamine series compound is preferably used in this invention. Typical examples of the color developing agent are 3-methyl-4-amino-N,N-diethylaniline, 3-methyl-4-amino-N-ethyl-N-$\beta$-hydroxyethylaniline, 3-methyl-4-amino-N-ethyl-N-$\beta$-methanesulfonamidoethylaniline, 3-methyl-4-amino-N-ethyl-N-$\beta$-methoxyethylaniline, and the sulfates, hydrochlorides, or p-toluenesulfonates thereof. These diamines are generally more stable in the form of the salts thereof than in the free state, and hence are preferably used in the form of salts.

The color developer generally contains a pH buffer such as the carbonate, borate, or phosphate of an alkali metal, and a development inhibitor or an antifoggant such as a bromide, an iodide, a benzimidazole, benzothiazole, and a mercapto compound. Also, if desired, the color developer may further contain a preservative such as hydroxylamine and a sulfite, an organic solvent such as triethanolamine, diethylene glycol, etc., a development accelerator such as benzyl alcohol, polyethylene glycol, a quaternary ammonium salt, an amine, etc., a dye forming coupler, a competing coupler, a nucleating agent such as sodium boronhydride, an auxiliary developing agent such as 1-phenyl-3-pyrazolidone, etc., a tackifier, a chelating agent such as aminopolycarboxylic acid, aminopolyphosphonic acid, alkylphosphonic acid, phosphonocarboxylic acid, etc., an antioxidant described in West German Patent Appliction (OLS) No. 2,622,950, etc.

When the color photographic material is a reversal color photographic material, a black and white development is usually performed before color development for processing the color photographic material. The black and white developer contains a dihydroxybenzene such as hydroquinone, etc., a 3-pyrazolidone such as 1-phenyl-3-pyrazolidone, etc., or an aminophenol such as N-methyl-p-aminophenol, etc., as a black and white developing agent solely or as a combination thereof.

After color development, the color photographic material is usually bleached. The bleach process may be performed simultaneously with or separate from a fix process. Furthermore, for quickening the photographic processing, a system of performing the blix (bleach-fix) process after bleach process may be employed.

As the bleaching agent, for example, compounds of a multivalent metal such as iron(III), cobalt(III), chromium(VI), copper(II), etc., peracids, quinones, nitroso compounds, etc., are used. Specific examples of the bleaching agent are ferricyanides; bichromates; organic complex salts of iron(III), or cobalt(III); complex salts of aminopolycarboxylic acids such as ethylenediaminetetraacetic acid, diethylenetriaminepentaacetic acid, nitrilotriacetic acid, 1,3-diamino-2-propanoltetraacetic acid, etc., or other organic acids such as citric acid, tartaric acid, malic acid, etc.; persulfates, manganates; nitrosophenol, etc. In these bleaching agents, ethylenediaminetetraacetic acid iron(III) salts, diethylenetriaminepentaacetic acid iron(III) salts and persulfates are preferred in the points of quick processing and causing less environmental pollution. Furthermore, the ethylenediaminetetraacetic acid iron(III) complex salts are particularly useful for an independent bleach liquid and a mono-bath type blix liquid.

For a pre-bath of the bleach liquid or the blix liquid, if necessary, a bleach accelerator can be used. Specific examples of the useful bleach accelerators are the compounds having a mercapto group or a disulfide group described in U.S. Pat. No. 3,893,858, West German Pat. Nos. 1,290,812 and 2,059,988, Japanese Patent Application (OPI) Nos. 32736/78, 57831/78, 37418/78, 65732/78, 72623/78, 95630/78, 95631/78, 104232/78, 124424/78, 141623/78, 28426/78, Research Disclosure, RD No. 17129 (July 1978), etc., thiazolidine derivatives described in Japanese Patent Application (OPI) No. 140129/78, the thiourea derivatives described in Japanese Patent Publication No. 8506/70, Japanese Patent Application (OPI) Nos. 20832/77, 32735/78, U.S. Pat. No. 3,706,561, etc.; the iodides describe in West German Pat. No. 1,127,715, Japanese Patent Application (OPI) No. 16235/83, the polyethylene oxides described in West German Pat. Nos. 966,410, 2,748,430, etc., the polyamine compounds described in Japanese Patent Publication No. 8836/70, the compounds described in Japanese Patent Application (OPI) Nos. 42434/74, 59644/74, 94927/78, 35727/79, 26506/80, and U.S. Pat. No. 4,446,225, and iodide ions and bromide ions. In these materials, the compounds having a mercapto group or a disulfide group are preferred from the viewpoint of having high accelerating effect and the compounds described in U.S. Pat. No. 3,893,858, West German Pat. No. 1,290,812, and Japanese Patent Application (OPI) No. 95630/78 are particularly preferred. Moreover, the compounds described in U.S. Pat. No. 4,552,834 are also preferred.

These bleach accelerators may exist in the color photographic materials. The use of these bleach accelerators is particularly effective in the case of blixing a photographing (or in camera) color photographic materials.

As a fixing agent, there are thiosulfates, thiocyanates, thioethers series compounds, thioureas, iodides (large amount), etc., but thiosulfates are generally used.

The blix liquid or fix liquid may contain a preservative, and preferred examples of the preservative are sulfites, hydrogen sulfites, and carbonyl-hydrogensulfites addition products.

After the blix process or the fix process, the color photographic material is usually subjected to washing with water and/or a stabilization process. The processing liquid for the wash process and/or the stabilization process may further contain various compounds for precipitation prevention and saving water. Examples of these additives are water softeners such as inorganic phosphates, aminopolycarboxylic acids, organic aminopolyphosphonic acids, organic phosphoric acids, etc., for preventing the occurrence of precipitation, antibacterial agents and antifungal agents for preventing the generation of various kinds of bacteria, algae, and molds, metal salts susch as a magnesium salt, an aluminum salt, and a bismuth salt, surface active agents for reducing drying load and preventing uneven drying, and various kinds of hardening agents.

Furthermore, the compounds described in L. E. West, *Photographic Science Engineering*, Vol. 6, 344–359 (1965) may be added to the processing liquid for the wash process and the stabilization process. In this case, chelating agents and antifungal agents are particularly effective.

The wash process is generally performed by a countercurrent wash system using two or more tanks for saving water. Furthermore, in place of the wash process, a multistage countercurrent stabilization process as described in Japanese Patent Application (OPI) No. 8543/82 may be employed. In this process, 2 to 9 countercurrent tanks are required.

To the stabilization liquid, various kinds of compounds are added for stabilizing the color images formed in addition to the aforesaid additives. Typical examples of such additives include various buffers for adjusting the pH (e.g., pH of 3 to 9) of the photographic layers (e.g., borates, metaborates, borax, phosphates, carbonates, potassium hydroxide, sodium hydroxide, aqueous ammonia, monocarboxylic acid, dicarboxylic acid, polycarboxylic acid, and a combination thereof) and aldehydes such as formaldehyde, etc.

Other examples of additives are chelating agents (e.g., inorganic phosphoric acid, aminopolycarboxylic acids, organic phosphoric acids, organic phosphonic acids, aminopolyphosphonic acids, phosphonocarboxylic acids), sterilizers (e.g., benzoisothiazolinone, isothiazolone, 4-thiazolinebenzimidazole, halogenated phenol, sulfanylamide, benzotriazole, etc.), surface active agents, fluorescent whitening agents, hardening agents, etc. They can be used singly or as combinations of the same kinds of additives or different kinds of additives.

Also, as a post-processing layer pH controlling agent, various ammonium salts such as ammonium chloride, ammonium nitrate, ammonium sulfate, ammonium phosphate, ammonium sulfite, ammonium thiosulfate, etc., are preferably added to the processing liquid.

In the case of for typical photographic use color photographic materials, the ordinary wash-stabilization process after fixing can be replaced by the above-described water saving water system for the wash process and stabilization process. In this case, when the magenta coupler is a two-equivalent coupler, formaldehyde, e.g., in the form of a formalin solution, may not be used for the stabilization liquid.

The processing time for the wash process and stabilization process in this invention depends upon the kind of the color photographic material and the processing condition thereof, but is usually from 20 seconds to 10 minutes, preferably from 20 seconds to 5 minutes.

The color photographic material of this invention may contain therein a color developing agent for simplifying and quickening the processing. For incorporating in the photographic materials, the precursors for a color developing agent are preferably used.

Examples of these precursors include the indoaniline series compounds described in U.S. Pat. No. 3,342,597, the Schiff base type compounds described in U.S. Pat. No. 3,342,599, *Research Disclosure*, RD No. 14850 (August 1976), and ibid., RD No. 15159 (November 1976), the aldol compounds described in *Research Disclosure*, RD No. 13924, the metal complexes described in U.S. Pat. No. 3,719,492, the urethane series compounds described in Japanese Patent Application (OPI) No. 135628/78, and the various salt type precursors described in Japanese Patent Application (OPI) Nos. 6235/81, 16133/81, 59232/81, 67842/81, 83734/81, 83735/81, 83736/81, 89735/81, 81837/81, 54430/81, 106241/81, 107236/81, 97531/82 and 83565/82.

The silver halide color photographic materials of this invention may contain therein various kinds of 1-phenyl-3-pyrazolidones for accelerating the color development. Typical examples of these additives are described in Japanese Patent Application (OPI) Nos. 64339/81, 144547/82, 211147/82, 50532/83, 505356/83, 50533/83, 50534/83, 50535/83 and 115438/83.

The various processing liquids in this invention are used at a temperature of from 10° C. to 50° C. The temperature of from 33° C. to 38° C. is standard, but a higher temperature may be employed for quickening the processing, or a lower temperature may be employed for improving the quality of color images and improving the stability of processing liquids. Furthermore, for the saving of silver in the color photographic materials, a process of using cobalt intensification or the hydrogen peroxide intensification described in West German Pat. No. 2,226,770 or U.S. Pat. No. 3,674,499 may be employed.

The various processing tanks which are used for processing the color photographic materials of this invention may be equipped with a heater, a temperature sensor, a liquid level sensor, a circulation pump, a filter, a floating lid, a squeegee, etc.

Also, in the case of performing continuous processing, a constant finish is obtained by using each replenisher for each processing liquid to prevent the deviation of the liquid composition. The amount of each replenisher can be reduced to a half or less than a half of a standard amount of replenisher for reducing costs.

The invention is now described in more detail by referring to the following examples.

In addition, in the following examples, the yellow couplers C-1 and C-2 described in U.S. Pat. No. 3,933,501, the couplers C-3 and C-4 described in U.S. Pat. No. 4,401,752, the coupler C-5 of the same kind as those described in Japanese Patent Application (OPI) No. 174839/84, the coupler C-6 described in U.S. Pat. No. 4,511,649, the yellow coupler C-7 of the same kind as those described in U.S. Pat. No. 4,022,620, the coupler C-8 described in U.S. Pat. No. 4,587,207, and the yellow couplers C-9 and C-10 described in Japanese Patent Application (OPI) No. 174839/84 were used as comparison couplers, which are shown below.

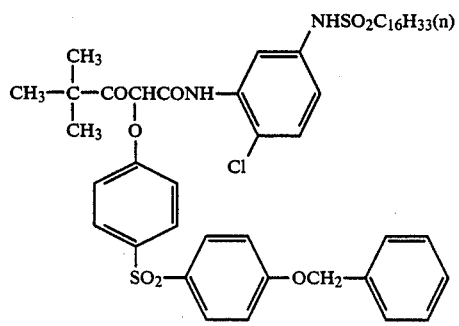

C-1

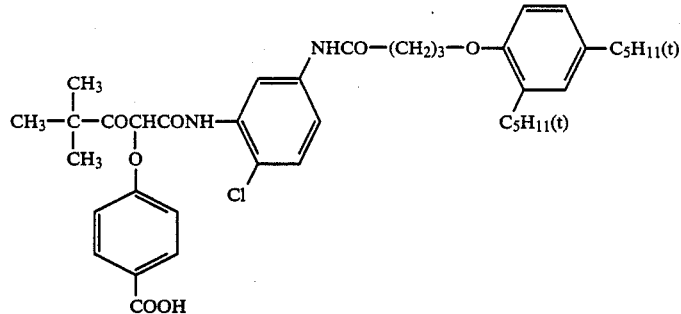
C-2
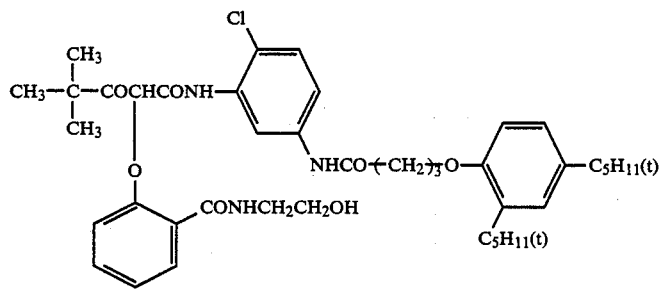
C-3
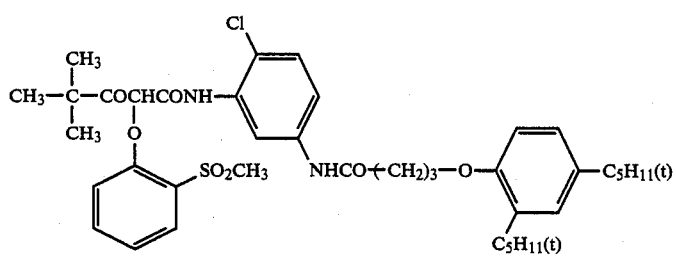
C-4
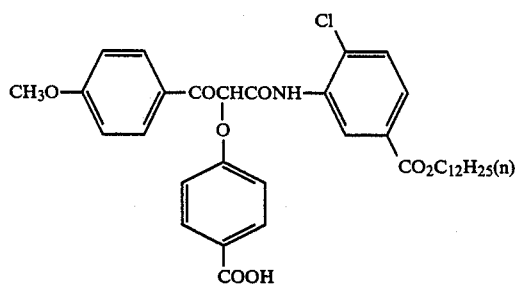
C-5
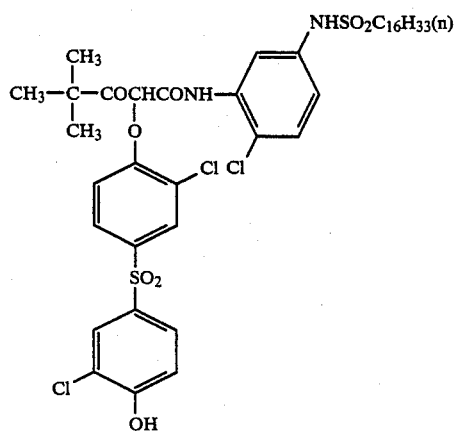
C-6

-continued

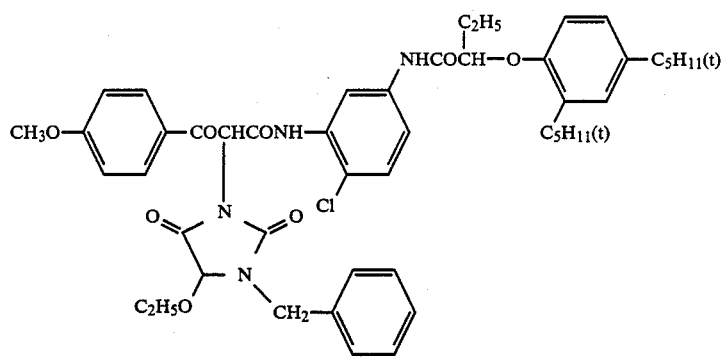
C-7

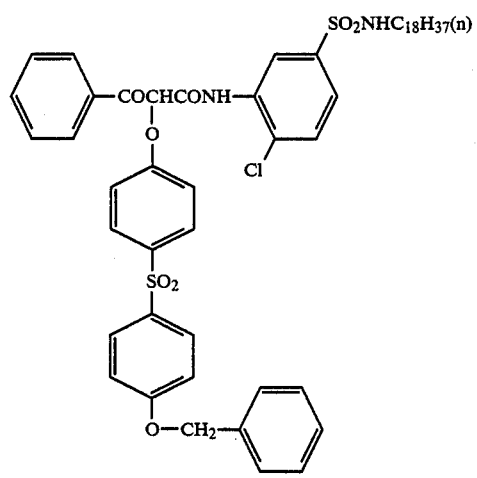
C-8

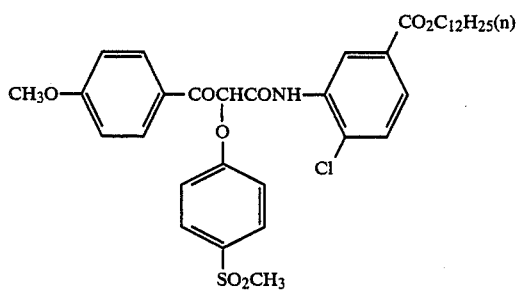
C-9

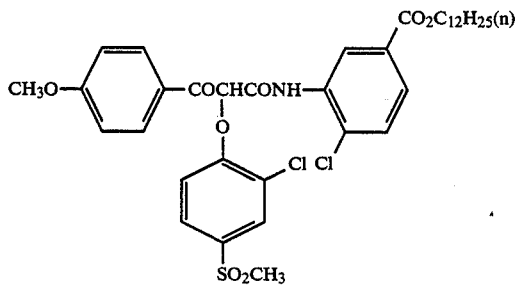
C-10

EXAMPLE 1

For evaluating the effectiveness of the yellow couplers of this invention that are represented by formula (I) described above, Samples 101 to 116 were prepared by forming each of the emulsion layers described below on a triacetyl cellulose support having a subbing layer.

The coating composition for each emulsion layer was prepared by dissolving each of the couplers in this invention and the comparison couplers shown above in ethyl acetate together with tricresyl phosphate (ratio of tricresyl phosphate/coupler=0.2 by weight), dispersing the solution in an aqueous gelatin solution by emulsification, and adding the emulsified dispersion to a siliver halide emulsion.

(1) Emulsion Layer:
Negative Working Silver Iodobromide   $9.0 \times 10^{-3}$ mol/m$^2$
Emulsion (grain size: 1.2 μm)         as silver
Coupler (shown in Table 1 below)      $1.1 \times 10^{-3}$ mol/m$^2$
Tricresyl Phosphate (weight ratio to

-continued

| | |
|---|---|
| the coupler is 0.2) | |
| Gelatin | 2.5 g/m² |
| (2) Protective Layer: | |
| 2,4-Dichloro-6-hydroxy-s-triazine Sodium Salt | 0.05 g/m² |
| Gelatin | 1.3 g/m² |

Each of the samples thus prepared was imagewise exposed through a step wedge and processed by the following processing steps. The density of the samples thus processed was measured by blue light and the results were evaluated by the sensitometric data. That is, the sensitometric curve of color density of log (exposure amount) was plotted and the samples were compared and evaluated by the maximum density (Dmax), the gamma ($\gamma$) value, and the reciprocal of the exposure amount required for giving the density of relative sensitivity of (fog+0.2), with that of Sample 101 being defined as 1.00. The results obtained are shown in Table 1 below.

The photographic processing used above was performed at 38° C. in the following steps.

| | |
|---|---|
| Color Development | 3 min. 15 sec. |
| Bleach | 6 min. 30 sec. |
| Wash | 2 min. 10 sec. |
| Fix | 4 min. 20 sec. |
| Wash | 3 min. 15 sec. |
| Stabilization | 1 min. 05 sec. |

The compositions of the processing liquids used for the aforesaid processing steps were as follows.

| | |
|---|---|
| Color Developer: | |
| Diethylenetriaminepentaacetic Acid | 1.0 g |
| 1-Hydroxyethylidene-1,1-diphosphonic Acid | 2.0 g |
| Sodium Sulfite | 4.0 g |
| Potassium Carbonate | 30.0 g |
| Potassium Bromide | 1.4 g |
| Potassium Iodide | 1.3 mg |
| Hydroxylamine Sulfate | 2.4 g |
| 4-(N—Ethyl-N—β-hydroxyethylamino)-2-methylaniline Sulfate | 4.5 g |
| Water to make | 1 liter |
| | pH 10.0 |
| Bleach Liquid: | |
| Ethylenediaminetetraacetic Acid Ferric Ammonium Salt | 100.0 g |
| Ethylenediaminetetraacetic Acid Di-sodium Salt | 10.0 g |
| Ammonium Bromide | 150.0 g |
| Ammonium Nitrate | 10.0 g |
| Water to make | 1 liter |
| | pH 6.0 |
| Fix Liquid: | |
| Ethylenediaminetetraacetic Acid Di-sodium Salt | 1.0 g |
| Sodium Sulfite | 4.0 g |
| Aqueous Solution of Ammonium Thiosulfate (70%) | 175.0 ml |
| Sodium Hydrogensulfate | 4.6 g |
| Water to make | 1 liter |
| | pH 6.6 |
| Stabilization Liquid: | |
| Formalin (40 wt % formaldehyde) | 2.0 ml |
| Polyoxyethylene-p-mononyl Phenyl Ether (Average polymerization degree 10) | 0.3 g |
| Water to make | 1 liter |

TABLE 1

| Sample No. | Coupler | Dmax | $\gamma$ | Relative Sensitivity | Fog |
|---|---|---|---|---|---|
| 101 (Comparison) | C-1 | 0.82 | 1.07 | 1.00 | 0.05 |
| 102 (Comparison) | C-2 | 0.58 | 0.76 | 0.69 | 0.05 |
| 103 (Comparison) | C-3 | 1.14 | 1.25 | 1.08 | 0.06 |
| 104 (Comparison) | C-4 | 1.03 | 1.16 | 1.02 | 0.07 |
| 105 (Comparison) | C-5 | 1.24 | 1.18 | 1.07 | 0.08 |
| 106 (Comparison) | C-6 | 1.12 | 1.24 | 1.09 | 0.06 |
| 107 (Comparison) | C-7 | 1.37 | 1.29 | 1.12 | 0.07 |
| 108 (Comparison) | C-8 | 1.35 | 1.25 | 1.11 | 0.08 |
| 109 (Comparison) | C-9 | 1.23 | 1.19 | 1.19 | 0.09 |
| 110 (Comparison) | C-10 | 1.27 | 1.22 | 1.22 | 0.08 |
| 111 (Invention) | (1) | 1.37 | 1.31 | 1.31 | 0.08 |
| 112 (Invention) | (3) | 1.35 | 1.30 | 1.30 | 0.07 |
| 113 (Invention) | (4) | 1.46 | 1.43 | 1.43 | 0.09 |
| 114 (Invention) | (7) | 1.44 | 1.41 | 1.41 | 0.08 |
| 115 (Invention) | (15) | 1.49 | 1.45 | 1.45 | 0.09 |
| 116 (Invention) | (25) | 1.37 | 1.38 | 1.38 | 0.08 |

From the results shown in Table 1, it can be seen that the samples using the couplers in this invention are excellent in coloring property and have a high sensitivity as compared with the samples using the comparison couplers.

EXAMPLE 2

For evaluating the effectiveness of the coupler of this invention, a multilayer color photographic material (Sample 201) having the following layers on a cellulose triacetate film support was prepared. Each coating amount of the silver halide emulsion means a coating amount as silver.

| | |
|---|---|
| Layer 1: Antihalation Layer: | |
| Black Colloid Silver | 0.18 g/m² |
| Ultraviolet Absorbent U-1 | 0.12 g/m² |
| Ultraviolet Absorbent U-2 | 0.17 g/m² |
| Tricresyl Phosphate | 0.01 g/m² |
| Dibutylphthalate | 0.01 g/m² |
| Gelatin | 0.48 g/m² |
| Layer 2: Interlayer: | |
| 2,5-Di-t-pentadecylhydroquinone | 0.18 g/m² |
| Coupler Cp-7 | 0.11 g/m² |
| Silver Iodobromide Emulsion (silver iodide: 1 mol %; mean grain size: 0.07 μm) | 0.15 g/m² |
| Tricresyl phosphate | 0.1 g/m² |
| Gelatin | 1.0 g/m² |
| Layer 3: 1st Red-Sensitive Emulsion Layer: | |
| Silver Iodobromide Emulsion (silver iodide: 6 mol %; mean grain size: 0.5 μm) | 0.72 g/m² |
| Sensitizing Dye I | 7.0 × 10⁻⁵ mol per mol of silver |
| Sensitizing Dye II | 2.0 × 10⁻⁵ mol per mol of silver |
| Sensitizing Dye III | 2.8 × 10⁻⁴ mol per mol of silver |
| Sensitizing Dye IV | 2.0 × 10⁻⁵ mol per mol of silver |
| Coupler Cp-1 | 0.020 g/m² |
| Coupler Cp-2 | 0.093 g/m² |
| Coupler Cp-3 | 0.31 g/m² |
| Coupler Cp-4 | 0.010 g/m² |
| Tricresyl Phosphate | 0.1 g/m² |
| Dibutylphthalate | 0.2 g/m² |
| Gelatin | 1.2 g/m² |
| Layer 4: 2nd Red-Sensitive Emulsion Layer: | |
| Silver Iodobromide Emulsion (silver iodide: 8 mol %; mean grain size: 0.8 μm) | 1.6 g/m² |
| Sensitizing Dye I | 5.2 × 10⁻⁵ mol per mol of silver |
| Sensitizing Dye II | 1.5 × 10⁻⁵ mol per mol of silver |

| | |
|---|---|
| Sensitizing Dye III | $2.1 \times 10^{-4}$ mol per mol of silver |
| Sensitizing Dye IV | $1.5 \times 10^{-4}$ mol per mol of silver |
| Coupler Cp-1 | 0.051 g/m² |
| Coupler Cp-2 | 0.10 g/m² |
| Coupler Cp-3 | 0.061 g/m² |
| Coupler Cp-4 | 0.005 g/m² |
| Coupler Cp-5 | 0.046 g/m² |
| Tricresyl Phosphate | 0.06 g/m² |
| Dibutylphthalate | 0.12 g/m² |
| Gelatin | 1.3 g/m² |
| Layer 5: 3rd Red-Sensitive Emulsion Layer: | |
| Silver Iodobromide Emulsion (silver iodide: 14 mol %; mean grain size: 1.4 μm) | 1.6 g/m² |
| Sensitizing Dye I | $4 \times 10^{-5}$ mol per mol of silver |
| Sensitizing Dye II | $1.2 \times 10^{-5}$ mol per mol of silver |
| Sensitizing Dye III | $1.8 \times 10^{-4}$ mol per mol of silver |
| Sensitizing Dye IV | $1.2 \times 10^{-5}$ mol per mol of silver |
| Coupler Cp-1 | 0.02 g/m² |
| Coupler Cp-2 | 0.03 g/m² |
| Coupler Cp-5 | 0.05 g/m² |
| Tricresyl Phosphate | 0.02 g/m² |
| Dibutylphthalate | 0.06 g/m² |
| Gelatin | 1.6 g/m² |
| Layer 6: Intermediate Layer | |
| 2,5-Di-t-pentadecylhydroquinone | 0.03 g/m² |
| Tricresyl Phosphate | 0.05 g/m² |
| Dibutylphthalate | 0.05 g/m² |
| Gelatin | 1.0 g/m² |
| Layer 7: 1st Green-Sensitive Emulsion Layer | |
| Silver Iodobromide Emulsion (silver iodide: 4 mol %; mean grain size: 0.4 μm) | 1.2 g/m² |
| Sensitizing Dye V | $3.8 \times 10^{-4}$ mol per mol of silver |
| Sensitizing Dye VI | $3.0 \times 10^{-5}$ mol per mol of silver |
| Sensitizing Dye VII | $1.2 \times 10^{-4}$ mol per mol of silver |
| Coupler Cp-6 | 0.29 g/m² |
| Coupler Cp-7 | 0.040 g/m² |
| Coupler Cp-8 | 0.055 g/m² |
| Coupler Cp-9 | 0.054 g/m² |
| Tricresyl Phosphate | 0.26 g/m² |
| Gelatin | 0.7 g/m² |
| Layer 8: 2nd Green-Sensitive Emulsion Layer | |
| Silver Iodobromide Emulsion (silver iodide: 6 mol %; mean grain size: 0.8 μm) | 1.5 g/m² |
| Sensitizing Dye V | $2.7 \times 10^{-4}$ mol per mol of silver |
| Sensitizing Dye VI | $2.1 \times 10^{-5}$ mol per mol of silver |
| Sensitizing Dye VII | $8.5 \times 10^{-5}$ mol per mol of silver |
| Coupler Cp-6 | 0.25 g/m² |
| Coupler Cp-7 | 0.013 g/m² |
| Coupler Cp-8 | 0.009 g/m² |
| Coupler Cp-9 | 0.010 g/m² |
| Tricresyl Phosphate | 0.25 g/m² |
| Gelatin | 1.1 g/m² |
| Layer 9: 3rd Green-Sensitive Emulsion Layer | |
| Silver Iodobromide Emulsion (silver iodide: 10 mol %; mean grain size: 1.4 μm) | 1.5 g/m² |
| Sensitizing Dye V | $3.0 \times 10^{-4}$ mol per mol of silver |
| Sensitizing Dye VI | $2.4 \times 10^{-5}$ mol per mol of silver |
| Sensitizing Dye VII | $9.5 \times 10^{-5}$ mol per mol of silver |
| Coupler Cp-10 | 0.070 g/m² |
| Coupler Cp-7 | 0.013 g/m² |
| Tricresyl Phosphate | 0.40 g/m² |
| Gelatin | 1.7 g/m² |
| Layer 10: Yellow Filter Layer | |
| Yellow Colloid Silver | 0.04 g/m² |
| 2,5-Di-t-pentadecylhydroquinone | 0.031 g/m² |
| Gelatin | 0.9 g/m² |
| Layer 11: 1st Blue-Sensitive Emulsion Layer | |
| Silver Iodobromide Emulsion (silver iodide: 6 mol %; mean grain size: 0.4 μm) | 0.32 g/m² |
| Coupler Cp-3 | 0.95 g/m² |
| Coupler Cp-11 | 0.030 g/m² |
| Tricresyl Phosphate | 0.80 g/m² |
| Gelatin | 2.0 g/m² |
| Layer 12: 2nd Blue-Sensitive Emulsion Layer | |
| Silver Iodobromide Emulsion (silver iodide: 10 mol %; mean grain size: 1.0 μm) | 0.40 g/m² |
| Coupler Cp-3 | 0.25 g/m² |
| Tricresyl Phosphate | 0.17 g/m² |
| Sensitizing Dye VIII | $2.2 \times 10^{-4}$ mol per mol of silver |
| Gelatin | 0.8 g/m² |
| Layer 13: 3rd Blue-Sensitive Emulsion Layer | |
| Silver Iodobromide Emulsion (silver iodide: 14 mol %; mean grain size: 2.3 μm) | 1.00 g/m² |
| Coupler Cp-11 | 0.30 g/m² |
| Tricresyl Phosphate | 0.25 g/m² |
| Sensitizing Dye VIII | $2.3 \times 10^{-4}$ mol per mol of silver |
| Gelatin | 1.2 g/m² |
| Layer 14: 1st Protective Layer | |
| Ultraviolet Absorbent U-1 | 0.14 g/m² |
| Ultraviolet Absorbent U-2 | 0.22 g/m² |
| Gelatin | 1.0 g/m² |
| Layer 15: 2nd Protective Layer | |
| Polymethyl Methacrylate Particles (diameter: 1.5 μm) | 0.05 g/m² |
| Silver Iodobromide Emulsion (silver iodide: 2 mol %; mean grain size: 0.07 μm) | 0.30 g/m² |
| Gelatin | 0.7 g/m² |

Further, the gelatin hardening agent and the surface active agent are added to the composition for each layer.

Then, the samples (Samples 202 and 203) of this invention were also prepared by the following manners.

Sample 202:

Sample 202 was prepared by following the same procedure as in the case of preparing Sample 201, except that Coupler C-3 for Layer 11 and Layer 12 of Sample 201 was replaced by an equimolar amount of Coupler (4) of formula (I) for use in this invention.

Sample 203:

Sample 203 was prepared by the same manner as Sample 202 while adjusting the amounts of Coupler (4) of this invention and tricresyl phosphate in Layers 11 and 12 of Sample 202 so that the scratch hardness thereof by a diamond stylus of 0.1 mm in tip diameter became the same as that of Sample 201. In this case, the coated amounts of Coupler (4), tricresyl phosphate and gelatin were 0.68 g/m², 0.57 g/m² and 1.4 g/m², respectively for Layer 11 and 0.18 g/m², 0.12 g/m² and 0.6 g/m², respectively for Layer 12.

These samples were imagewise exposed, processed as in Example 1, the densities of color images obtained were measured using a blue filter, and the results obtained are shown in Table 2 below. Also, the samples were exposed through pattern for measuring MTF (modulation transfer frequency) using a green filter and the MTF value was measured on each sample. The measurement of the MTF value was performed by the method described in Mees, *The Theory of the Photographic Process*, 3rd Edition (published by Macmillan Co.). The results obtained are shown in Table 2.

In addition, the compounds used for preparing the samples in this example are shown below.

TABLE 2

| Sample No. | Relative Sensitivity* of Blue-Sensitive Layer | MTF Value of Green-Sensitive Layer (20 cycles/mm) |
|---|---|---|
| 201 (Comparison) | 0.00 | 0.53 |
| 202 (Invention) | +0.19 | 0.54 |
| 203 (Invention) | +0.04 | 0.57 |

*Relative value of the logarithm of the reciprocal of the exposure amount giving a density of fog + 0.5 with that of Sample 201 being defined as 0.00.

From the results shown in Table 2, it can be clearly seen that Sample 202 had a higher sensitivity than that of Comparison Sample 201 and also Sample 203, wherein the photographic performance and the layer strength were adjusted to match with those of the comparison sample and is excellent in sharpness.

polymer of

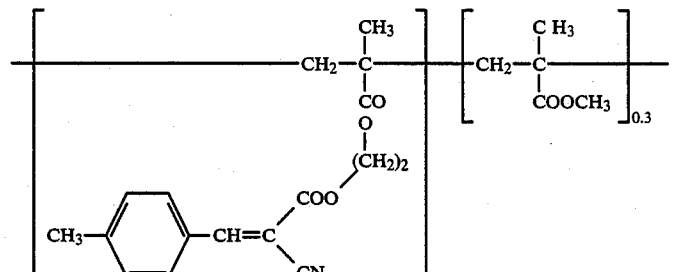

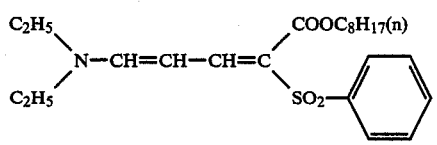

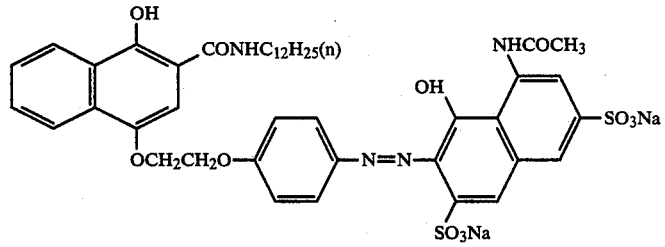

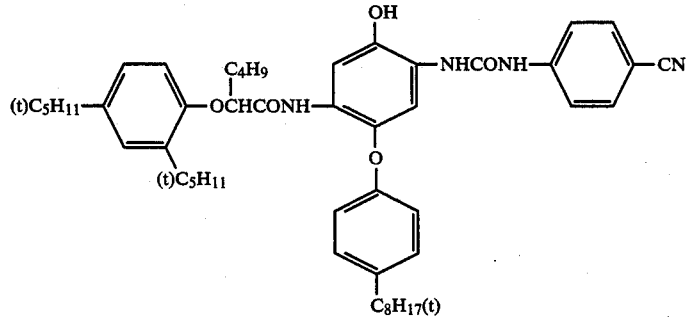

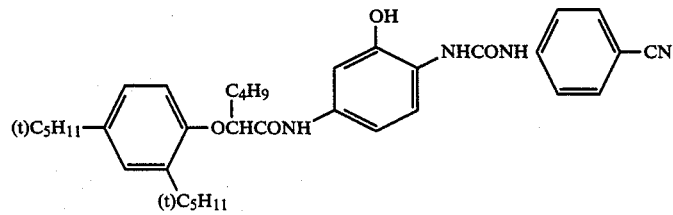

Cp-4
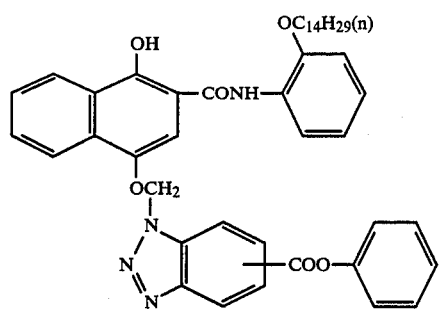
Cp-5
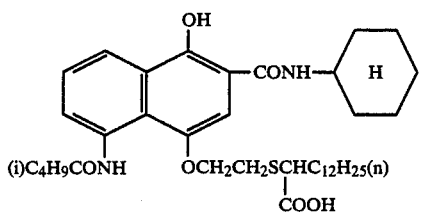
polymer of
Cp-6
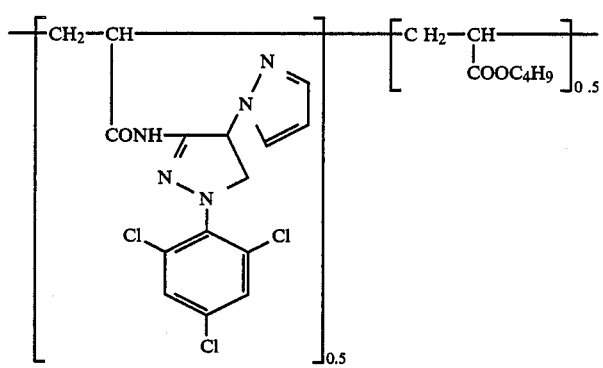
Cp-7
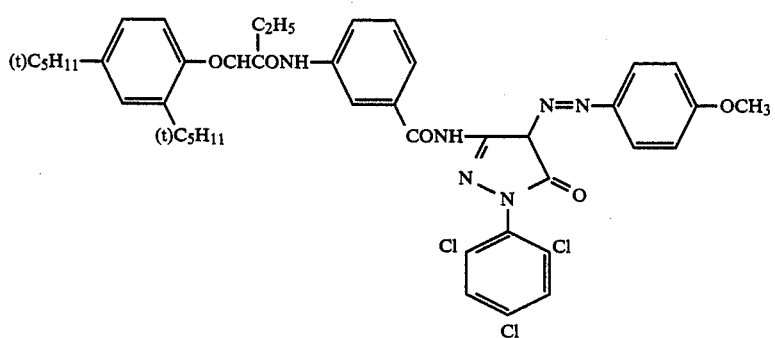
Cp-8
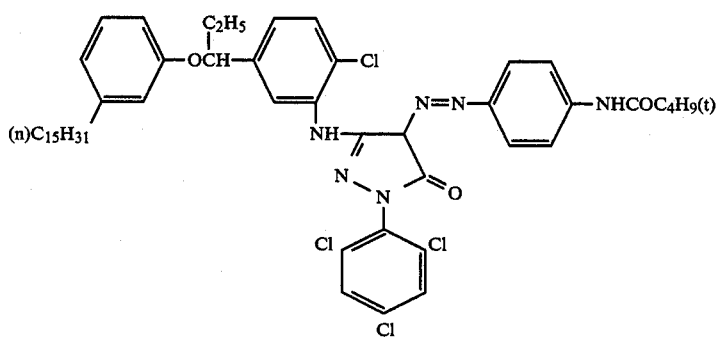

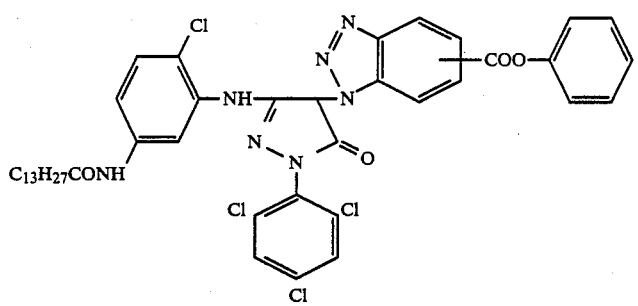
Cp-9
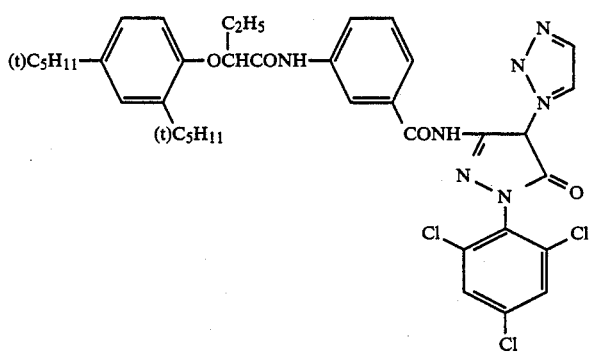
Cp-10
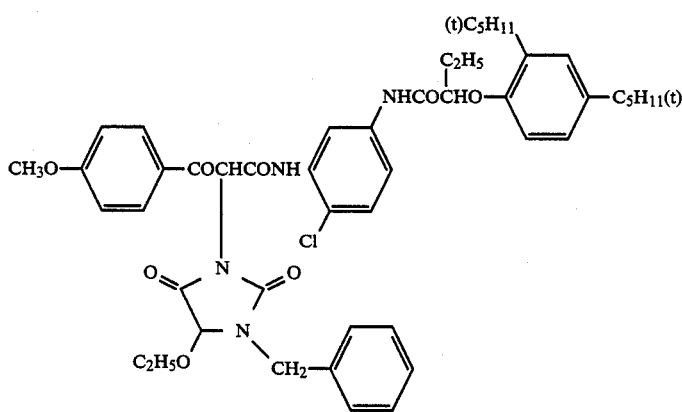
Cp-11
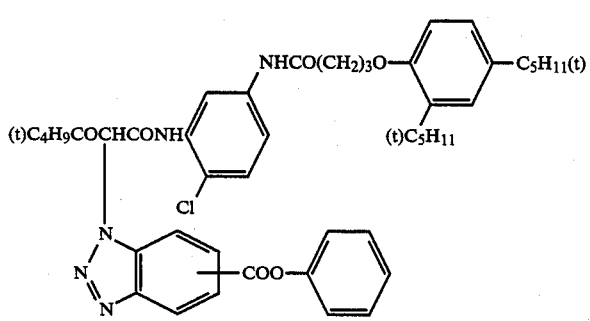
Cp-12
Gelatin Hardening Agent
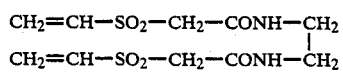
H-1

-continued

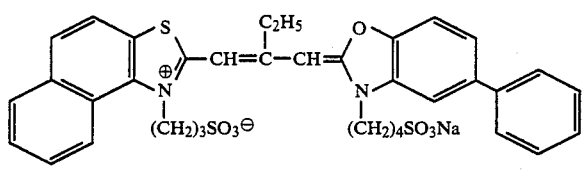

Sensitizing Agent I

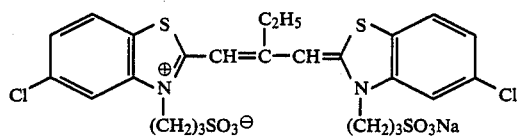

Sensitizing Agent II

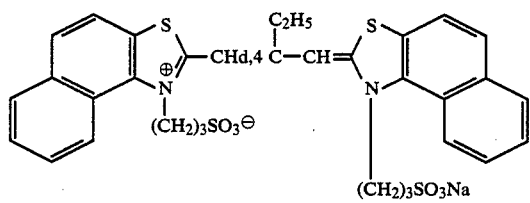

Sensitizing Agent III

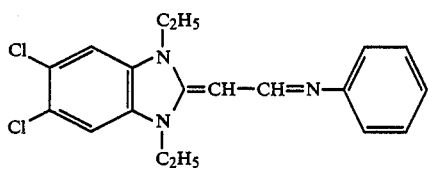

Sensitizing Agent IV

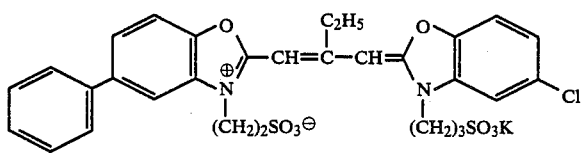

Sensitizing Agent V

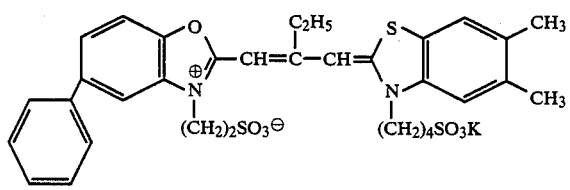

Sensitizing Agent VI

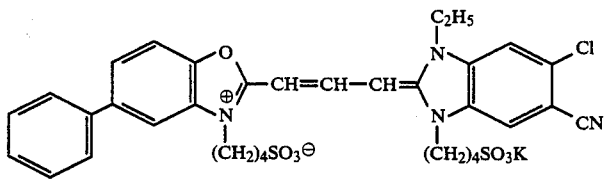

Sensitizing Agent VII

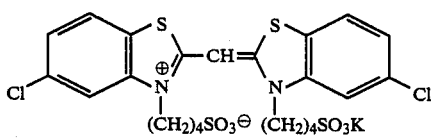

Sensitizing Agent VIII

As described above, the yellow two-equivalent couplers for use in this invention have an excellent coloring property and provide high contrast. Accordingly, the amount of the coupler can be reduced in the case of using the coupler in this invention, and hence the couplers are very useful as yellow couplers for color negative photographic films having high sensitivity and which provide high image quality.

While the invention has been described in detail and with reference to specific embodiments thereof, it will be apparent to one skilled in the art that various changes and modifications can be made therein without departing from the spirit and scope thereof.

What is claimed is:

1. A silver halide color photographic material comprising a support having thereon at least a silver halide emulsion layer containing a compound represented by formula (I)

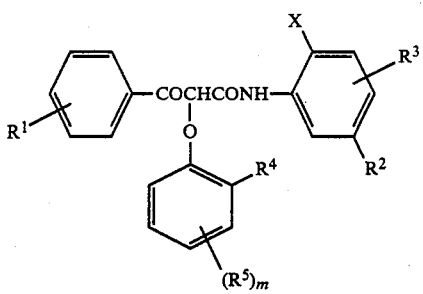

(I)

wherein $R^1$ represents a hydrogen atom, an alkyl group, an alkoxy group, a halogen atom, an alkoxycarbonyl group, a carbamoyl group, a carbonamido group, a sulfonamido group, or a sulfamoyl group; $R^2$ represents a carbonamido group, a sulfonamido group, an alkoxycarbonyl group, a carbamoyl group, or a sulfamoyl group; $R^3$ represents a hydrogen atom, a chlorine atom, a methyl group, a methoxy group or an ethoxy group; X represents a chlorine atom, a methoxy group or an ethoxy group; $R^4$ represents a methylsulfonyl group, an ethylsulfonyl group, or a phenylsulfonyl group; $R^5$ represents a hydrogen atom, a halogen atom, a halogen-substituted alkyl group, a nitro group, a cyano group, a carbamoyl group, a sulfamoyl group, an alkylsulfonyl group, an acyl group, an alkoxycarbonyl group, an aryloxycarbonyl group, an alkoxy group, an aryloxy group, a carbonamido group, or a sulfonamido group; provided that at least one of said $R^1$, $R^2$, and $R^5$ is a non-diffusible group; and m represents an integer of from 0 to 4.

2. A silver halide color photographic material as in claim 1, wherein at least one of said $R^1$, $R^2$, and $R^5$ is a non-diffusible group comprising a polymeric chain.

3. A silver halide color photographic material as in claim 1, wherein the coupler represented by formula (I) exists in the form of an oligomer, a homopolymer, or a copolymer containing a recurring unit represented by formula (II)

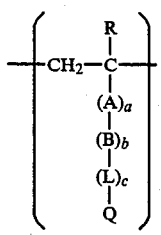

(II)

wherein R represents a hydrogen atom, an alkyl group having from 1 to 4 carbon atoms, or a chlorine atom; A represents —CONH—, —COO—, or a substituted or unsubstituted phenylene group; B represents a substituted or unsubstituted alkylene group, a substituted or unsubstituted phenylene group, or a substituted or unsubstituted aralkylene group; L represents —CONH—, —NHCONH—, —NHCOO—, —NHCO—, —OCONH—, —NH—, —COO—, —OCO—, —CO—, —O—, —S—, —SO$_2$—, —NHSO$_2$—, or —SO$_2$NH—; Q represents a yellow coupler residual group formed by releasing hydrogen atoms other than the hydrogen atom of the methine group from the compound represented by formula (I); and a, b, and c each represents 0 or 1.

4. A silver halide color photographic material as in claim 3, wherein said coupler represented by formula (I) forms a copolymer, and said copolymer comprises an acrylic acid ester, methacrylic acid ester, or a maleic acid ester.

5. A silver halide color photographic material as in claim 1, wherein the coupler represented by formula (I) is contained in an amount of from $1 \times 10^{-7}$ to 1 mol per mol of silver in the same emulsion laiyer or in an emulsion layer adjacent to the layer containing the compound represented by formula (I).

6. A silver halide color photographic material as in claim 4, wherein the coupler represented by formula (I) is contained in an amount of from $1 \times 10^{-7}$ to 1 mol per mol of silver in the same emulsion layer or in an emulsion layer adjacent to the layer containing the compound represented by formula (I).

7. A silver halide color photographic material as in claim 5, wherein the coupler represented by formula (I) is contained in an amount of from $1 \times 10^{-7}$ to 1 mol per mol of silver in the same emulsion layer or in emulsion layer adjacent to the layer containing the compound represented by formula (I).

8. A silver halide color photographic material as in claim 6, wherein the coupler represented by formula (I) is contained in an amount of from $1 \times 10^{-7}$ to 1 mol per mol of silver in the same emulsion layer or in an emulsion layer adjacent to the layer containing the compound represented by formula (I).

9. A silver halide color photographic material as in claim 1, wherein the coupler represented by formula (I) is contained in an amount of from $1 \times 10^{-3}$ to 0.5 mol per mol of silver in the same emulsion layer or in an emulsion layer adjacent to the layer containing the compound represented by formula (I).

10. A silver halide color photographic material as in claim 4, wherein the coupler represented by formula (I) is contained in an amount of from $1 \times 10^{-3}$ to 0.5 mol per mol of silver in the same emulsion layer or in an emulsion layer adjacent to the layer containing the compound represented by formula (I).

11. A silver halide color photographic material as in claim 5, wherein the coupler represented by formula (I) is contained in an amount of from $1 \times 10^{-3}$ to 0.5 mol per mol of silver in the same emulsion layer or in an emulsion layer adjacent to the layer containing the compound represented by formula (I).

12. A silver halide color photographic material as in claim 6, wherein the coupler represented by formula (I) is contained in an amount of from $1 \times 10^{-3}$ to 0.5 mol per mol of silver in the same emulsion layer or in an emulsion layer adjacent to the layer containing the compound represented by formula (I).

* * * * *